/

US009015922B2

(12) United States Patent
Ganey

(10) Patent No.: US 9,015,922 B2
(45) Date of Patent: Apr. 28, 2015

(54) BONE IMPLANTS AND METHOD OF MANUFACTURE

(71) Applicant: Vivex Biomedical, Inc., Marietta, GA (US)

(72) Inventor: Timothy Ganey, Tampa, FL (US)

(73) Assignee: Vivex Biomedical, Inc., Marietta, GA (US)

( * ) Notice: Subject to any disclaimer, the term of this patent is extended or adjusted under 35 U.S.C. 154(b) by 222 days.

(21) Appl. No.: 13/737,043

(22) Filed: Jan. 9, 2013

(65) Prior Publication Data

US 2013/0125382 A1    May 23, 2013

Related U.S. Application Data

(62) Division of application No. 13/303,944, filed on Nov. 23, 2011, now Pat. No. 8,414,654.

(51) Int. Cl.
*A61F 2/28* (2006.01)
*A61F 2/44* (2006.01)
(Continued)

(52) U.S. Cl.
CPC .. *A61F 2/44* (2013.01); *Y10T 29/49* (2015.01); *Y10T 29/49746* (2015.01); *A61F 2/28* (2013.01); *A61F 2/30767* (2013.01);
(Continued)

(58) Field of Classification Search
CPC ..... A61F 2/44; A61F 2/30767; A61F 2/4455; A61F 2/28; A61F 2002/30981; A61F 2/3094; A61F 2002/3097; A61F 2002/2835; A61F 2310/0023; A61F 2002/3098; A61F 2002/30604; A61F 2310/00976; A61F 2002/30062; A61F 2002/3096; A61F 2002/30904; A61F 2002/30; Y10T 29/49746; Y10T 29/49; A61B 17/80; A61B 17/7098
USPC ......... 29/527.1; 623/23.5, 16.11, 23.6, 23.55, 623/23.72–23.76, 17.11; 514/8.2; 424/423
See application file for complete search history.

(56) References Cited

U.S. PATENT DOCUMENTS 3,852,045 A    12/1974 Wheeler et al.
5,112,354 A    5/1992 Sires
(Continued)

FOREIGN PATENT DOCUMENTS

EP    2338530    6/2011
WO    9939757    8/1999
(Continued)

OTHER PUBLICATIONS

St. John T.A., et al., Physical and Monetary Costs Associated With Autogenous Bone Graft Harvesting, Am. Journal of Orthopedics; 32:18-23, 2003.
(Continued)

*Primary Examiner* — David Bryant
*Assistant Examiner* — Jun Yoo
(74) *Attorney, Agent, or Firm* — David L. King

(57) ABSTRACT

An implant device for humans or mammals has a body structure having an exposed surface and one or more selected portions of the exposed surface having a bone formation enhancing 3-dimensional pattern. The exposed surface can be on exterior portions of the body structure or internal portions of the body structure or both. The one or more selected portions of the exposed portions having the bone formation enhancing 3-dimensional patterns are in the external exposed surfaces or in the internal exposed surfaces or both internal and external exposed surfaces.

17 Claims, 8 Drawing Sheets

(51) Int. Cl.
*A61F 2/30* (2006.01)
*A61B 17/80* (2006.01)
*A61B 17/70* (2006.01)

(52) U.S. Cl.
CPC .... *A61F 2/4455* (2013.01); *A61F 2002/30838* (2013.01); *A61F 2002/30904* (2013.01); *A61F 2002/3092* (2013.01); *A61F 2002/30925* (2013.01); *A61F 2002/3093* (2013.01); *A61F 2002/30971* (2013.01); *A61F 2002/4475* (2013.01); *A61B 17/7098* (2013.01); *A61B 17/80* (2013.01); *A61F 2/3094* (2013.01); *A61F 2002/2835* (2013.01); *A61F 2002/30062* (2013.01); *A61F 2002/3038* (2013.01); *A61F 2002/30604* (2013.01); *A61F 2002/3096* (2013.01); *A61F 2002/3097* (2013.01); *A61F 2002/3098* (2013.01); *A61F 2002/30981* (2013.01); *A61F 2310/00017* (2013.01); *A61F 2310/00023* (2013.01); *A61F 2310/00976* (2013.01)

(56) References Cited

U.S. PATENT DOCUMENTS

| | | | |
|---|---|---|---|
| 5,282,861 | A | 2/1994 | Kaplan |
| 5,665,118 | A * | 9/1997 | LaSalle et al. ............... 623/23.5 |
| 6,419,491 | B1 | 7/2002 | Ricci |
| 7,018,418 | B2 | 3/2006 | Amrich et al. |
| 7,901,462 | B2 | 3/2011 | Yang et al. |
| 2001/0039454 | A1* | 11/2001 | Ricci et al. ................... 623/23.5 |
| 2003/0059742 | A1 | 3/2003 | Webster et al. |
| 2003/0125739 | A1 | 7/2003 | Bagga et al. |
| 2006/0129161 | A1* | 6/2006 | Amrich et al. .................. 606/85 |
| 2010/0036502 | A1 | 2/2010 | Svrluga |
| 2010/0040334 | A1* | 2/2010 | Shannon et al. ................ 385/89 |
| 2010/0137990 | A1* | 6/2010 | Apatsidis et al. .......... 623/17.16 |

FOREIGN PATENT DOCUMENTS

| | | |
|---|---|---|
| WO | 2006044832 | 4/2006 |
| WO | 2008115160 | 9/2008 |

OTHER PUBLICATIONS

Olson G.B., Computational Design of Hierarchically Structured Materials, Science; 277: 1237-1242, 1997.
Liao H., et al., Response of rat osteoblast-like cells to microstructured model surfaces in vitro, Biomaterials 24: 649-54, 2003.
Clover J. and Dodds R.A., Integrin subunit expression by human osteoblasts and osteoclasts in situ and in culture, J. Cell Sci; 103: 267-271, 1994.
Ingber D.E., Cellular Tensegrity: Exploring How Mechanical Changes in the Cytoskeleton Regulate Cell Growth, Migration, and Tissue Pattern during Morphogenesis, Int. Rev. Cytol.; 150: 173-224, 1994.
Meazzini MC et al., Osteoblast Cytoskeletal Modulation in Response to Mechanical Strain In Vitro, J. Orthop. Res.; 16: 170-180, 1998.
Ingber D.E., Tensegrity: The Architectural Basis of Cellular Mechanotransduction, Annu. Rev. Physiol.; 59: 575-599, 1997.
Bindermann I., et al., The Transduction of Mechanical Force into Biochemical Events in Bone Cells May Involve Activation of Phospholipase A2, Calcif Tissue Int.; 42: 261-266, 1988.
Somjen D., et al., Bone Remodeling Induced by Physical Stress Is Prostaglandin E2 Mediated, Biocim. Biophys. Acta; 627: 91-100, 1980.
Kurtz, Steven M; Devine, John N; Peek biomaterials in trauma, orthopedic and spinal implants, Aug. 7, 2007, Biomatenals, 28, 4845-4869.
Nikolovski J., et al., FASEB J.; 17: 455-7, 2003.
Rozengurt E., et al., Cyclic AMP: A mitogenic signal for Swiss 3T3 cells, J. Cell Biol.; 78: 4392-4396, 1981.
Shen V., et al., Prostaglandins Change Cell Shape and Increase Intercellular Gap Junctions in Osteoblasts Cultured From Rat Fetal Calvaria, J. Bone Miner Res.; 1: 2443-249, 1986.
Chen C.S., et al., Geometric Control of Cell Life and Death, Science; 276: 1425-1428, 1997; Edmondson A.C., Bosten, 1987.
Jee W.S.S., et al., Effects of spaceflight on trabecular bone in rats, Am. J. Physiol.; 244: R310-R314, 1983.
Zerath E., et al., Effects of spaceflight on bone mineralization in the rhesus monkey, J. Appl. Physiol.; 81: 194-200, 1996.
Backup P.K., et al., Spaceflight results in reduced mRNA levels for tissue-specific proteins in the musculoskeletal system, Am. J. Physiol.; 266: E567-E573, 1994.
Holick MF, Perspective on the Impact of Weightlessness on Calcium and Bone Metabolism, Bone; 22: 105S-111S, 1998.
Caillot-Augusseas A., Lafage-Proust MH et al., Bone formation and resorption biological markers in cosmonauts during and after a 180-day spaceflight (Euromir 95), Clin. Chem.; 44: 578-585, 1998.
Sampath T.K. and Reddi A.H., Distribution of bone inductive proteins in mineralized and demineralized extracellular matrix, Biochem Biophys. Res. Commun.; 119: 949-54, 1984.
Ganey T.M., et al., Trabecular Parameters in Whale: Examining Naive Trabecular Conformation; 44th Annual Meeting, New Orleans, Louisiana, Orthopaedic Research Society, Mar. 16-19, 1998.
Harris S.A., et al., Effects of Orbital Spaceflight on Human Osteoblast Cell Physiology and Gene Expression, Bone 20(4) 26: 325-31, 2000.
Reddi A.H. and Huggins C.B., Proc. Soc. Exp. Biol. Med.; 143: 634-637, 1973.
Sampath T.K. and Reddi A.H., Importance of Geometry of the Extracellular Matrix in Endochondral Bone Differentiation, J. Cell. Biol.; 98: 2192-2197, 1984.
Borden M., et al., Structural and human cellular assessment of a novel microsphere-based tissue engineered scaffold for bone repair, Biomaterials; 24: 597-609, 2003.
Koob T.J., et al., Biocompatibility of NDGA-polymerized collagen fibers I. Evaluation of cytotoxicity with tendon fibroblasts in vitro, J. Biomed. Mat. Res.; 56: 31-39, 2001.
Koob T.J. and Hernandez D.J., Material properties of polymerized NDGA-collagen composite fibers: development of biologically based tendon constructs, Biomaterials; 23: 203-212, 2002.
Suzuki F. Roles of cartilage matrix proteins, chondromodulin-I and -II, in endochondral bone formation: a review. Connect Tissue Res. 1996;35(1-4):303-7.
Gamradt SC, Lieberman JR. Genetic modification of stem cells to enhance bone repair. Ann Biomed Eng. Jan. 2004;32(1):136-47.
Sammarco VJ, Chang L. Modern issues in bone graft substitutes and advances in bone tissue technology. Foot Ankle Clin. Mar. 2002;7(1):19-41.
Department of Health and Human Services, 2. Jul. 2002; http://www.fda.gov/cdrh/mda/does/p000058.pdf.
Sikavitsas V.I., et al., Formation of three-dimensional cell/polymer constructs for bone tissue engineering in a spinner flask and a rotating wall vessel bioreactor, J. Biomed. Mat. Res.; 62: 136-146, 2002.
Jaiswal N., et al., Osteogenic Differentiation of Purified, Culture-Expanded Human Mesenchymal Stem Cells In Vitro, J. Cell Biochem.; 64: 295-312, 1997.
West D.C., et al., A Simplified in Situ Solubilization Procedure for the Determination of DNA and Cell Number in Tissue Cultured Mammalian Cells. Anal. Biochem.; 147: 289-295, 1985.
Koob T.J., et al., Biocompatibility of NDGA-polymerized collagen fibers II. Attachment, proliferation, and migration of tendon fibroblasts in vitro, J. Biomed. Mat. Res.; 56: 40-48, 2001.
Tavakoli M., et al; The use of power beams in surface modification, Medical Device Technology, vol. 18 No. 1, Jan.-Feb. 2007: TWI Ltd, 2007.
Elias Carlos Nelson, Titanium dental implant surfaces, Materia (Rio J.) vol. 15 No. 2 Rio de Janeiro 2010, online version ISSN 1517-7076.
Alekhin A.P., et al; Structural properties of the titanium dioxide thin films grown by atomic layer deposition at various numbers of reaction cycles, Applied Surface Science 257 (2010) 186-191.

(56) References Cited

OTHER PUBLICATIONS

Ogden, John A, Skeletal Injury in the Child, Third Edition, Springer, pp. 5-6.

Yeh, Chih-Ko and Rodan, Gideon A, Tensile Forces Enhance Prostaglandin E Synthesis in Osteoblastic Cells Grown on Collagen Ribbons, Dept of Oral Biology, University of Connecticut Health Center, Calcified Tissue International (1984) 36: S67-S71.

* cited by examiner

BONE IMPLANTS AND METHOD OF MANUFACTURE

RELATED APPLICATIONS

This application is a divisional of U.S. Ser. No. 13/303,944 filed on Nov. 23, 2011.

FIELD OF THE INVENTION

The present invention relates to bone implants, and more particularly to an improved implant and an improvement in the manufacture of such implants.

BACKGROUND OF THE INVENTION

The use of skeletal implants is common in surgical repairs. Implants are employed in a variety of procedures such as spinal repair, knees, hips or shoulders and others. A common and most important feature of many implants is the integration of the implant into the skeletal structure. Mechanical fasteners, sutures and adhesives and other ways of affixing the device to the bone structure are used. These implants can be fashioned from human bone or other biological material or alternatively can be made from implantable grade synthetic plastics or metals like stainless steel, titanium or the alloys of metals suitable for implantation.

One of the benefits of these plastic or metal implants is the strength and structure can be specifically designed to be even more durable than the bone being replaced.

As mentioned, one concern is properly securing the implant in place and insuring it cannot be dislodged or moved after repair. One of the best solutions to this issue is to allow the surrounding bone structure to grow around the implant and in some cases of hollow bone implants to allow new bone growth to occur not only around, but throughout the implant as well to achieve interlocked connectivity.

This is not particularly easy in many of the metal implants or hard plastic implants. In fact, the surface structure of the implant material is often adverse to bone formation. On some implant surfaces this may in fact be a desirable characteristic, but in those procedures where new bone growth formation is desirable this is problematic.

It is therefore an object of the present invention to provide an improved implant device that encourages new bone growth formation at selected surfaces of the device. The selected surfaces can be some or all external or internal exposed surface features of the implant device. The device with exposed surfaces that have selected surfaces for bone growth formation can be prepared by the methods as described below.

SUMMARY OF THE INVENTION

An implant device for humans or mammals has a body structure having an exposed surface and one or more selected portions of the exposed surface having a bone formation enhancing 3-dimensional pattern. The exposed surface can be on exterior portions of the body structure or internal portions of the body structure or both. The one or more selected portions of the exposed portions having the bone formation enhancing 3-dimensional patterns are in the external exposed surfaces or in the internal exposed surfaces or both internal and external exposed surfaces.

The 3-dimensional pattern is made of a substantially continuous network having voids or indentations. The voids or indentations have a medium width of about 30-300 microns and at least 10 percent of said voids have a fractal dimension of at least 3 microns. The voids have a depth into the selected surface of about 150 microns or less. In a preferred embodiment the 3-dimensional pattern mimics a marine or sea mammal bone structure such as a whale or dolphin. The voids have a medium width of 500-800 microns in the open marrow regions of the implant device when formed as a trabecular bone structure.

The body structure is made of an implantable plastic or polymer or is made of a metal suitable for implanting in a human or mammal. The metal can be titanium or a titanium alloy or a stainless steel or a stainless steel alloy.

The body structure can be made of an implantable grade synthetic plastic, which is a thermoplastic or thermoset material. The plastic material can be any implantable grade material such as PEEK (polyether ether ketone), PEKK (polyether ketone ketone), polyethylene, ultra high molecular weight polyethylene, polyphenylsulfone, polysulfone, polythermide, acetal copolymer, polyester woven or solid or implantable grade lennite UHME-PE. The implant device may include anchoring holes to secure the device to the skeletal structure with fasteners or alternatively can simply be held in place by and between adjacent skeletal structures. The implant device can be built by additive fabrication through a process offering reproducible and reconcilable formation to the istropic domains inherent to the marine mammal cancellous bone. In such application, the internal structure is modeled for strength, neutralized for strain, and open to surface modification of its entire network of trabecular permutations.

DEFINITIONS

As used herein and in the claims:

"Exposed surface" means surfaces that are typically an outer or planar feature of 2-dimensions as used herein and throughout this description. "Exposed surface" means an outer skin or surface having a depth providing a 3-dimensional character, this depth being the distance the surface pattern penetrates into the body structure of the device to produce a repeatable pattern for enhancing bone formation on the implant device. The exposed surface might also include an open trabecular structure wherein the voids extend from the surface throughout the structure.

BRIEF DESCRIPTION OF THE DRAWINGS

The invention is described by way of example and with reference to the accompanying drawings in which:

FIG. 1A shows an implant device made according to the present invention.

FIG. 1B shows a first alternative embodiment made according to the present invention.

FIG. 1C shows a second alternative embodiment made according to the present invention.

FIG. 1D shows a third alternative embodiment made according to the present invention.

FIG. 1E shows a fourth alternative embodiment made according to the present invention.

FIG. 1F shows a fifth alternative embodiment made according to the present invention.

FIG. 1G shows a sixth alternative embodiment made according to the present invention.

FIG. 1H shows a seventh alternative embodiment made according to the present invention.

FIG. 1I shows an eighth alternative embodiment made according to the present invention.

FIG. 1J shows a ninth alternative embodiment made according to the present invention.

FIG. 1K shows a tenth alternative embodiment made according to the present invention.

DETAILED DESCRIPTION OF THE INVENTION

Figure 1:
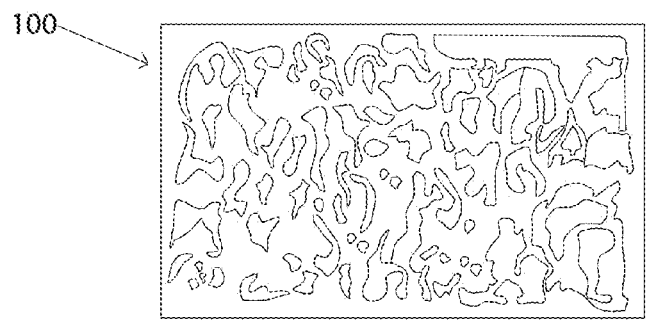
FIG. 1 shows a Type-I collagen matrix cut by free-electron laser to reproduce cancellous bone according to the state of the art.

Orthopaedic surgeons have been applying the principles of tissue engineering for years, transplanting and shifting matrices within patients to promote regenerative potential. The advent of new technology offers even greater promise and brings unbridled enthusiasm that full regenerative potential of tissue and whole organ systems can be achieved in the near future. While soft tissue repair can be managed by achieving scar tissue replacement, such outcome in most orthopaedic applications and indications would be insufficient. Bone requires tissue-specific composition attendant to its function for skeletal support. Formation of collagenous material alone, even if vascularized, will fail to meet the biophysical demands of repetitive skeletal loading and be inadequate.

Implicit in the goals of repairing bone are to achieve restitution of space, mechanical solidarity, and functional continuity. Often the biological signals do not provide sufficient stimulus to attain a full repair. Orthopedic interventions to alleviate fracture nonunion, pseudarthrosis, and scoliosis; bone defects due to congenital or developmental anomalies, infection, malignancy, or trauma often require bone grafting to augment the process of bone healing. The therapeutic goal of graft material is to omit compliance features such as strain tolerance, reduced stiffness, and attenuated strength, and instead promote primary, or membranous-type bone formation within the physical approximation of a graft material. Three basic components are required: osteoprogenitor cells, osteoinductive factors, and an osteoconductive matrix or scaffold.

Autologous cancellous bone remains to date the most effective graft material, where osteoinductivity, osteoconductivity, and a rich source of cells endow the material with not only biological activity but a degree of immunologic transparency as well. Because of complications and shortcomings associated with autogenous grafting that include limited quantity, donor-site morbidity, and more recently cost consideration (1), numerous alternative graft materials have been developed for orthopedic applications.

Available grafting substitutes include cancellous and cortical allograft bone, ceramics such as sintered coralline matrices, hydroxyapatite and tri-calcium phosphate, demineralized bone matrix, bone marrow, composite polymer grafts, and recently recombinant cytokines with collagen carriers. Complications include availability, cost, variable bioabsorption, brittleness, immune stimulation, and regulatory hurdles.

Future bio-engineering strategies will combine several favorable properties of the current items in an effort to achieve hybrid materials that support tissue differentiation without shielding capacity for integrated modeling. Ideally, new materials will provide tissue compatibility and minimize patient morbidity. The goal of this invention is to provide an implant that will be not only structurally enhancing but inductively optimum for bone formation. Relying on a defined pattern to promote conductivity, this manufactured implant has been designed to stimulate cell differentiation and bone regeneration, and be utilized as an orthotopic alternative to tissue transplantation.

The concept for manufactured implant depends on a capacity to achieve reproducible design in a geometric pattern on an exposed surface of the implant. Such implants will support osteoblast attachment and permit bone-specific matrix production. In light of anticipated rulings by the FDA for greater control of tissue products for transplantation, developing alternative materials with comparable osteoinductivity seems appropriate. Several features combine to make this proposal unique; first, the bone model for the architecture approximates an under-modeled mammal, using increased porosity to accelerate ingrowth; second, a unique cross-linking methodology reduces the bioabsorption rate of human collagen and effects a mechanically competent selected surface; and third, osteoblasts can be used to deposit a bone matrix onto the device that will make it osteoinductive. The controlled process is intended to take advantage of previous regulatory considerations of human collagen as a device. FDA approval for human collagen in combination with excipient material is not unprecedented.

The shape of the geometric pattern template is critical to the success of manufacturing. A central tenet of biomineralization is that nucleation, growth, morphology and aggregation of the inorganic crystals of bone are regulated by organized assemblies of organic macromolecules. The close spatial relationship of hydroxyapatite crystals with Type I collagen fibrils in the early stage of bone mineralization is a relevant example. It is equally evident that combining hydroxyapatite with protein does not render the macroscopic form of bone nor impart its characteristic properties. Unlike fabricated materials that can be developed from components with predictable properties, biological systems control desired properties by utilizing an intrinsic rationale that discriminates essential from non-essential factors. Living organisms avoid the geometric frustration of randomness by segregating structure that resonate function.

Although bone can appear de novo, it more often develops from accretion on a scaffold of matrix that contains appropriate vascular and compositional arrangement. As such, 3-dimensional patterns enhance osteoconductivity. Bone has significantly more matrix than cells, and cell regulation through anchorage dependent mechanisms is an established premise. Compensatory mechanisms for changing sensitivity to mechanical stimulation have been shown to undergo adaptive or kinetic regulation, likely tied directly to osteoblast attachment to immobilized molecules in the extracellular matrix (ECM). ECM molecules promote cell spreading by resisting cell tension, thereby promoting structural rearrangements within the cytoskeleton. Several lines of evidence suggest that tension or mechanical stretch exerts a direct positive effect on bone cells and bone cell differentiation through: 1.) activation of phospholipase A2, 2.) release of arachidonic acid; 3.) increased prostaglandin E synthesis; 4.) augmented cyclic adenosine monophosphate (cAMP) production; and 5.) expression of the bone-associated transcription factor CBFA-1. It has long been recognized that a sustained increase in the cellular level of cAMP constitutes a growth-promoting signal, and that prostaglandins directly effect a change in cell shape and increase intercellular gap junctions. Without a capacity for attachment and spreading, cells undergo apoptosis, or programmed cell death.

Bone withstands compressive loading by efficient distribution of internal tensile forces. Bone cells do however adhere to structures that can resist compression in order to spread, engaging osteoblast attachment, mineralization, and bone matrix organization as linked processes. Even though deformation at the tissue level might be evaluated as an ability to resist compression, force along individual trabeculae reflects an ordinate of new tension. Under normal cycles of development, increased mass conveys a progressive stimulus of tension to cells, gravity imposing a unidirectional vector to terrestrial life.

A sudden reduction in gravity imposes serious consequence to the skeleton. As shown by studies of astronauts, marked skeletal changes in the weight-bearing skeleton including a reduction in both cortical and trabecular bone formation, alteration in mineralization patterns, and disorganization of collagen and non-collagenous protein metabolism have been associated with microgravity. Each month of spaceflight results in a 1-2% reduction of bone mineral density that has been linked to down-regulated PTH (parathyroid hormone) and 1,25-dihydroxyvitamin D3 production. Indices from cosmonauts aboard Euromir 95 account bone atrophy to both a reduction in bone formation and increased resorption. PTH decreased (48%), as did bone alkaline phosphatase, osteocalcin, and type-I collagen propeptide. At the same time bound and free deoxypyridinoline and pro-collagen telopeptide increased. The chords of information establish a role for microgravity in uncoupling bone formation and enhancing resorption.

If exposure to microgravity demonstrates physiologic responses that mirror a reduction in trabecular tension, then would reciprocity of function be expected in bone that is modeled under microgravity and then exposed to normal gravitational force? Prolonged weightlessness, as experienced in space flight, effectively unloads the skeleton, relaxing tension on the trabeculae. In this manner, osteoblast physiology will be altered due to attachment perturbations. Conversely, a bioscaffold modeled in the form of tissue that has developed under microgravity, will experience an enhanced tensile loading sensation on individual trabeculae. This has the inventor of the present invention to predict that cells attached to this matrix will undergo a direct stimulus, and display enhanced osteoblast physiology as demonstrated in the mechanotransduction studies previously noted.

It is this invention's intent to duplicate the architecture of under-modeled cancellous bone, guided by the idea that a material later populated with bone cells will more quickly respond to the mechanical and biological roles of bone with subsequent loading. Because cancellous bone is a porous structure, its mechanical properties are dependent upon the distribution and arrangement of its structural elements, or trabeculae. Considering three-dimensional architecture to be critical to the mechanical integrity of trabecular bone, his work established the morphometry of under loaded marine mammal tissue. The rationale for this approach is based on the observation that pre-natal cancellous bone in humans has unique potential for rapid post-natal modeling, and that cell-culture studies performed during orbital space flight demonstrate significant osteoblast stimulation upon return to increased gravitational field. In the case of sea mammals, separate environment buoyancy suppresses loading variation, resulting in minimal secondary bone formation and modeling. Whale bone retains a primary trabecular structure and does not remodel according to standard parameters of mechanical adaptation. Trabecular morphology and osteocyte number are similar among commonly oriented blocks, while significant differences can be demonstrated between tissue sections studied in planes perpendicular to the axial length of bones (Table 1).

TABLE 1

| BIOPSY | BV/TV | BS/BV | TbTh | TbSp | TbN | Ost # |
|---|---|---|---|---|---|---|
| Cross | 17.71 | 14.98 | 135.16 | 631.70 | 1.33 | 230/mm² |
| Long | 24.54 | 8.67 | 231.05 | 710.98 | 1.06 | 150/mm² |

BV/TV—Bone Volume/Tissue Volume;
BS/BV—Bone Surface/Bone Volume;
TbTh—Trabecular Thickness = μm;
TbN—Trabecular Number;
Ost #—osteocyte cells per mm2.

Bone examined in longitudinal dimension demonstrated greater trabecular separation, thicker trabeculae, yet because of the lesser number of trabecula, still structured less bone surface per volume of tissue. Although bone surface to bone volume, trabecular thickness, and trabecular number followed predicted allometric extrapolation, bone volume was considerably less than that scaled for land mammals, and was reflected in greater trabecular separation and reduced trabecular number. It is this separation and thickness that provides a basis for bio-reactor cell culture and offer the chance to manufacture bone.

To best take advantage of the improved implant device of the present invention, it is believed that the selected 3-dimensional pattern can be applied on all or parts of the exposed interior or exterior surfaces assuming the method of preparing the surface permits, and that technology is also available to define a structural solid incorporating the porosity without reducing the loading capacity in the context of tensile stiffness.

For example, if an embossing technique is used wherein the pattern is pressed into the selected surfaces of the implant device then it is applied on suitable exposed exterior surfaces.

Similarly if the method of etching or engraving is used, the exterior surfaces can be easily prepared and some, but not necessarily all exposed internal surfaces can have a portion covered by the 3-dimensional pattern.

Figure 2:
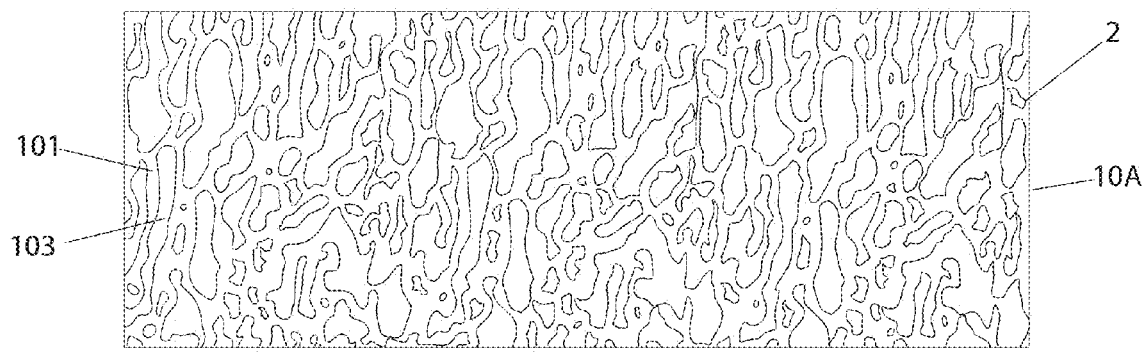
FIG. 2 shows a collagen scaffold or sheet representing cancellous bone according to the invention, wherein a tile pattern has been used.

As shown in FIG. 2, these 3-dimensional patterns 100A are most conveniently applied to thin layers 10A which can be collagen based layers 10A as disclosed in co-pending U.S. patent application Ser. No. 13/303,811 entitled "Bone Graft" filed on Nov. 23, 2011 concurrently with the present application which is incorporated by reference herein in its entirety. These thin implant layers 10A provide a maximum surface substantially planar exposed surface which can effectively achieve a 3-dimensional pattern 100A on one or both of the top or bottom surfaces a patterned sheet structure of scaffold 2. These layers 10A can be assembled to form 3-dimensional scaffolds which can form the body structure in part or all of an implant.

Figure 2A:
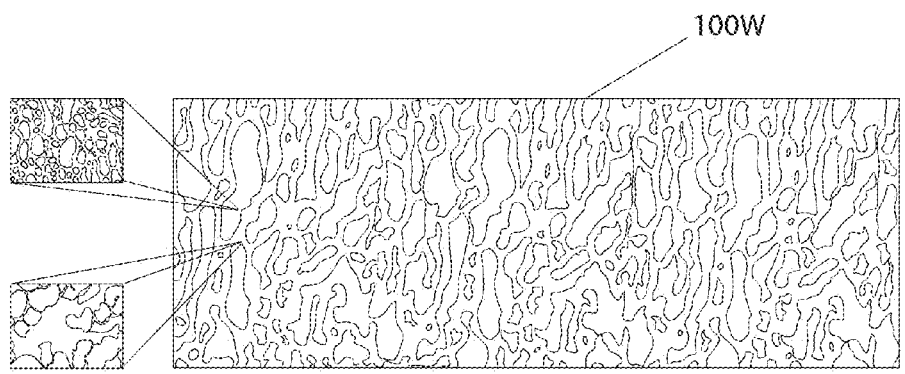
FIG. 2A is a photo reproduction of cancellous whale bone, the large portion being of the same scale as shown in FIG. 2, the upper left view being at scale, the lower left view being magnified.

As shown in FIG. 2, the sheet 2 with a pattern 100A is shown magnified at least 5 times to enable the 3-dimensional pattern to be more readily visible. The pattern as illustrated is proportionally accurate otherwise. With reference to FIG. 2A is a photo reproduction of cancellous whale bone, the large portion being of the same scale as shown in FIG. 2, the upper left view being at scale, the lower left view being magnified. This actual pattern 100W of whale bone closely resembles the reproduced 3-dimensional pattern 100A and clearly mimics this whale bone structure.

To better illustrate the pattern 100A, each device 10 is shown with the 3-dimensional pattern 100A illustrated as a magnified portion separate in a magnified circle and a reference line pointing to the exposed surface. It is understood this pattern 100A is very small and in order to visualize its appearance, this circle of the magnified surface 13 depicting the pattern 100A is provided. To try and illustrate the pattern 100A at true scale would result in the appearance of sandpaper of a fine grit similar to the skin of a shark. For this reason, the pattern 100A is shown separate and magnified, when in practice, the device 10 actually can have the entire exposed surface covered by the pattern 100A. The 3-dimensional pattern 100A is made of a substantially continuous network having voids or indentations. The voids or indentations have a medium width of about 30-300 microns and at least 10 percent of said voids have a fractal dimension of at least 3 microns. The voids have a depth into the selected surface of about 150 microns or less. In a preferred embodiment the 3-dimensional pattern mimics a marine or sea mammal bone structure such as a whale or dolphin. The voids have a medium width of 500-800 microns in the open marrow regions of the implant device when formed as a trabecular bone structure.

Figure 5:
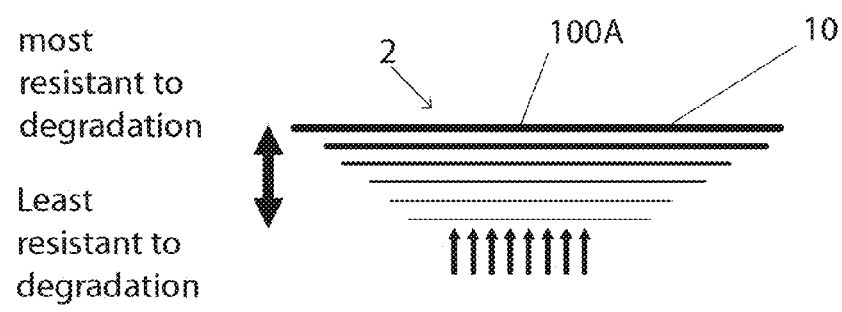
FIG. 5 is a schematic representation of a laminate structured sheet material having different (controlled) degradability.

In certain devices the layers 10A can be made of implantable grade plastics or metals which are assembled together in a laminate sheet structure 2 having the selected 3-dimensional pattern 100A on the surfaces of adjacent layers 10A. This is believed an ideal way to achieve enhanced new bone growth in the region of the implant as shown in FIG. 5.

Figure 7:
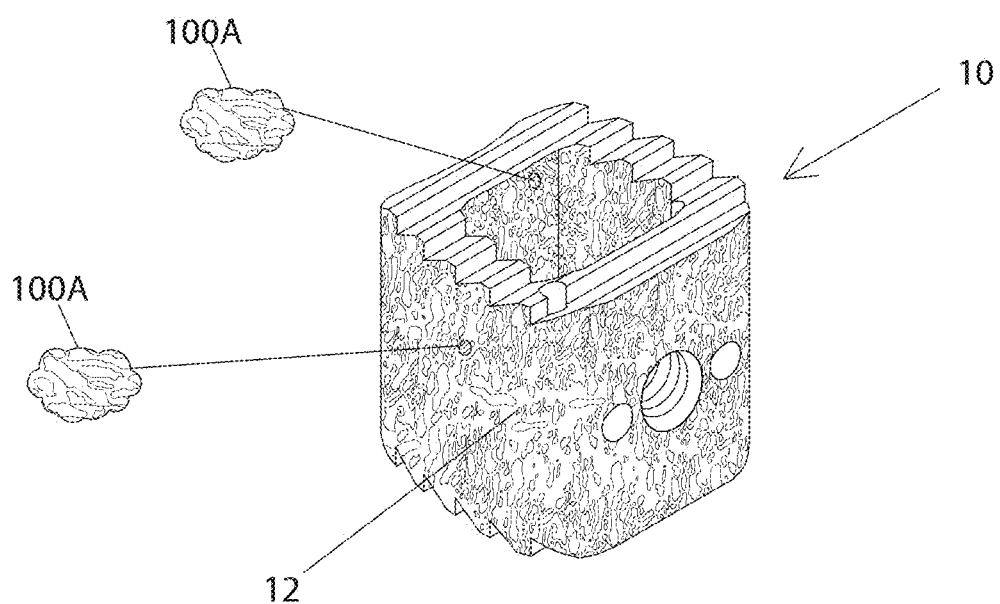
FIG. 7 is a perspective view of one of the exemplary devices of FIG. 1A with a pattern on the exposed surface made according to the present invention.
Figure 7A:
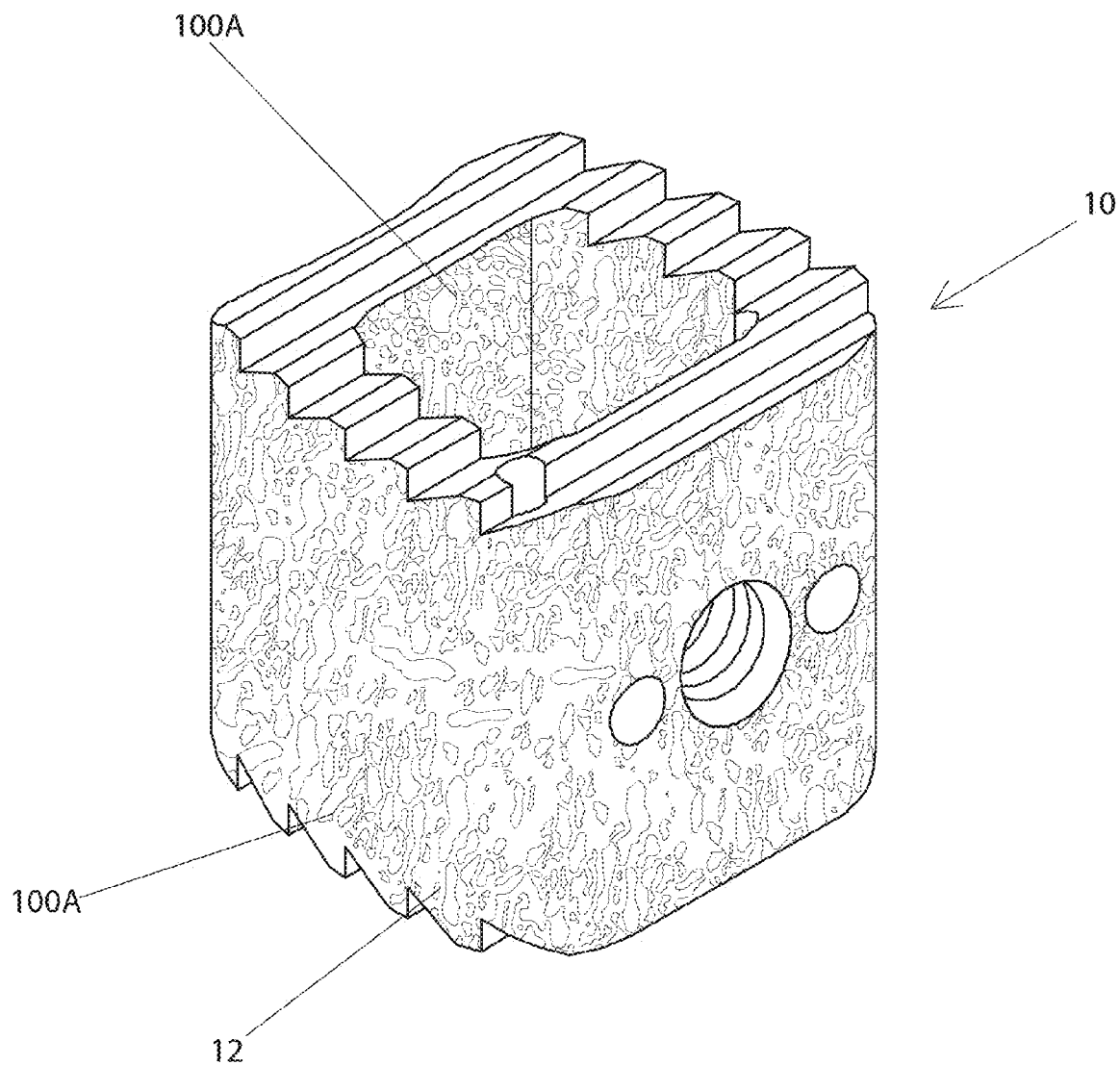
FIG. 7A is a perspective view taken from FIG. 7 of the exemplary device of FIG. 1A wherein the device has been magnified in size to match the scale of the pattern of FIG. 2.

Alternatively, the improved implant device 10 can be a molded, machined or otherwise manufactured 3-dimensional device having a specific body structure 12 with exposed surfaces 13 onto which the repeatable geometric 3-dimensional pattern 100A can be placed on selected portions of the exposed surface to create a continuous network of voids which will enhance bone formation, as shown in FIG. 7. With reference to FIG. 7A, the device 10 has been magnified in size such that the 3-dimensional pattern 100A is of the same scale as shown in FIG. 2 allowing for a better view of how the pattern is applied to the exposed surfaces 13. Exposed surfaces can be defined and developed throughout the implant based on manufacturing technique, for example, if the implant is made as an assembly of layers, the pattern can extend throughout the body structure of the device. Furthermore, additive fabrication technology with thermoplastic lasering might also be used to attest a shape from the molecular components of powdered ingredients.

It is most beneficial if the repeatable 3-dimensional geometric pattern can be achieved as part of the initial manufacture of the implant device 10 by imparting a negative onto the molding surfaces or in a cast of a sintered metal part. It must be appreciated that the size of the voids between the ridges 103 and channels 101 of the pattern 100A shown in the sheets 2 of FIG. 2 are extremely small and as a result such pattern formation to be repeatable in the surfaces 13 can be assured by a secondary procedure of embossing, etching, micropatterning or pressing onto an exposed surface 13 of the implant device 10. Chemical etching, while feasible, can be used with the understanding the implant 10 must be free if any residual chemical that could be adverse to bone formation. Plasma deposition can also be used to form the pattern on the exposed surfaces of the device. Plasma-enhanced chemical vapor deposition (PECVD) is a process used to deposit thin films from a gas state (vapor) to a solid state on a substrate.

Most importantly, in the preferred embodiment, the geometric 3-dimensional pattern 100A is selected to duplicate or at least closely mimic the pattern of a marine mammal such as a whale. While this pattern 100A is preferred, other similar patterns that approach the void percentage depth and shape of a human pre-natal cellular structure are also considered optimal alternatives. The main distinction of this surface pattern 100A is that it is repeatable. Conventional surface treatments that roughen a surface to improve chemical adhesion simply do not achieve this ability to enhance bone formation about an implant device. Whereas this repeatable pattern 100A has demonstrated this ability. Ideally, the implant device 10, once prepared with a suitable 3-dimensional pattern 100A, can be used in the surgical procedure for which it was designed without any alteration in the procedure with confidence that the prepared pattern surfaces 100A will facilitate new bone formation. Alterntiavely, more preferably, these improved implant devices 10 can be also treated with gels or coatings or sheets laden with bone formation enhancing cells which will find the patterned surfaces ideal for growth and adherence. Alternatively, the geometric 3-dimensional pattern 100A is selected to duplicate or at least closely mimic the pattern of a marine mammal such as a dolphin.

Once the geometric 3-dimensional pattern 100A is achieved in a reproducible manner on a selected surface of an implant device 10, it can be coated or otherwise treated with cells to enhance bone creation and bone formation in the selected areas of the pattern or alternatively, the implant device 10 can be simply implanted relying on the patient's tissue to attach and initiate bone formation de nova.

One interesting opportunity in the use of 3-dimensional patterns 100A is to produce a negative pattern and a positive pattern on adjacent structures. For example, a scaffold or sheet 2 as described in the above referenced co-pending application can have a negative pattern and the implant device 10 can have a positive pattern in a selected exposed surface 13. The two can be assembled into an abutting relation by wrapping the sheet 2 onto the device 10 to cause the mating surfaces to enhance bone formation as illustrated in FIG. 6.

It is important to appreciate the improved device provides a beneficial surface to facilitate bone creation more quickly than in the absence of the 3-dimensional patterns. Furthermore, unlike a surface texture or roughening to enhance chemical bonding, the selected geometric patterns mimic prenatal cancellous bone formation, which ideally, stimulates a biological response not otherwise appreciated or achieved in synthetic or metallic structures. The most common implants are load bearing devices with direction forces imparted due to the molding process. Isotropic structures are not bound in design by a vector of directional force. A biomaterial with no loading history supports integration that is singularly directed and substantially more efficient because it comes from a neutral state of loading, the forces guiding the new bone are biologically consistent with not the history of the material construction, but the combined geometry of the implant plus the regenerative potential of the construct. In instance, the intention of using the whale bone as a foundation material is that it has the same mechanical properties regardless of the direction of loading. This isotropy is a fundamental value to an inert prosthesis as it does not shield in any way the active loading signals during the fusion, or regenerative process. The integration is through the unit, not around the unit. As the PEEK material is inert, any preset conditions for its structure must be overcome and neutralized before material properties of the regenerative repair can be focused. The use of the pattern 100A mimics the whale bone and neutralizes these flow stresses in the exposed surface of the body structure 12 of the molded type such as PEEK device 10.

Figure 1B:
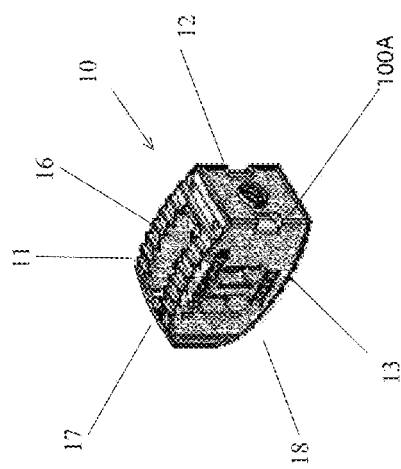
FIGS. 1A-1K are a number of perspective views of exemplary synthetic, metallic or a combination thereof which can additionally include a microceramic admixture with PEEK or PEKK or titanium implant devices that can be made according to the present invention.
Figure 1D:
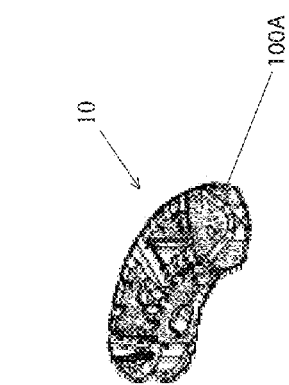
Figure 1A:
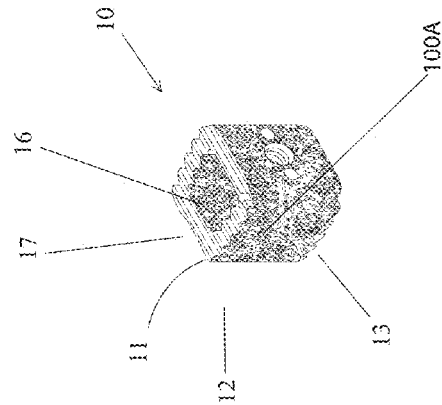
Figure 6:
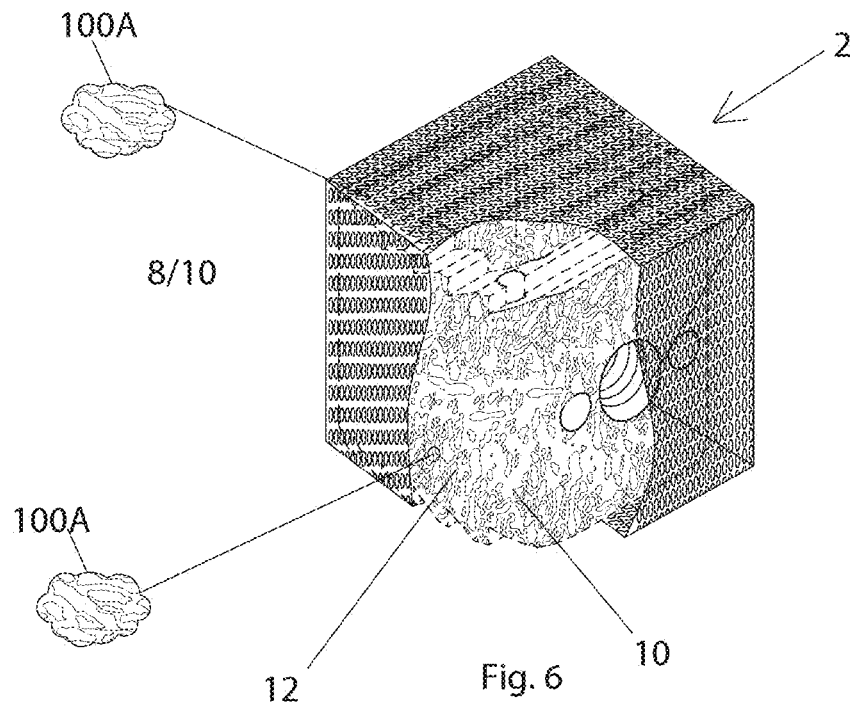
FIG. 6 is a perspective view of one of the exemplary devices of FIG. 1A with a pattern on the exposed surfaces and a wrapping of a sheet from FIG. 2.

The use of an implant device similar to that illustrated in FIGS. 1A, 6 and 7 shows a very open or exposed device which affords numerous exposed surfaces 13 as selected areas for applying the 3-dimensional pattern. The device 10 itself being open affords improved opportunity for bone formation internally and externally and therefore is highly complimentary to the concepts of pattern formation to enhance bone growth.

For purposes of the present invention, any device suitable for implanting having an exposed surface 13 onto which a bone formation enhancing pattern 100A is considered within the scope of the present invention, these include any skeletal implant including spine, hips, knees, shoulders, neck, feet, hands or any bone like repair implant. The shape of the body structure can be any shape where an exposed internal or external surface is available to apply 3-dimensional bone growth enhancing patterns. The implant device can be of any shape including spheres, hemispheres, ovals, disks, rings, rectangles, squares, solid or hollow tubes or the like.

Figure 1C:
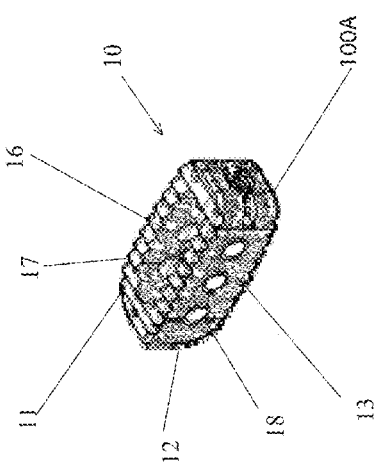
Figure 1F:
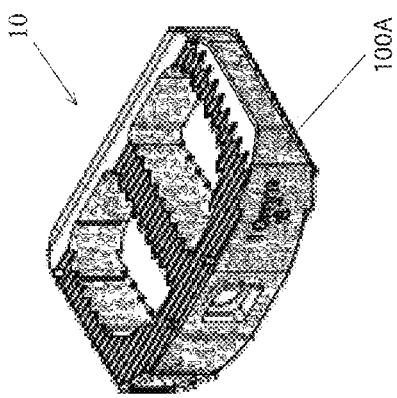
Figure 1H:
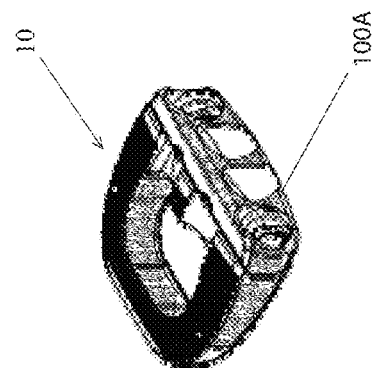
Figure 1E:
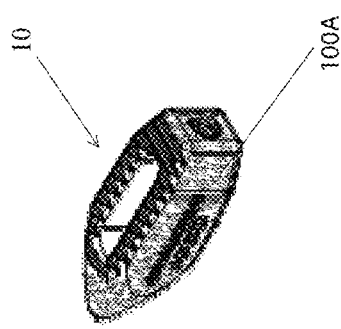
Figure 1G:
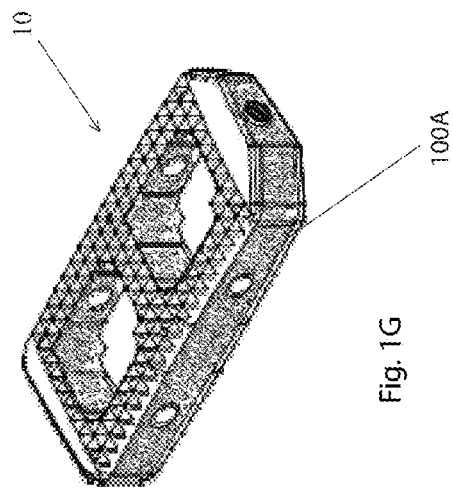
Figure 1J:
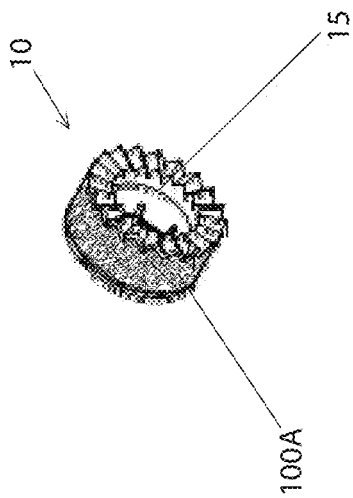
Figure 1I:
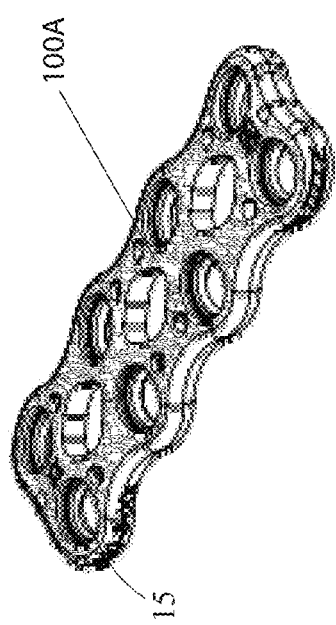
Figure 1K:
Figures 3A, 3B:
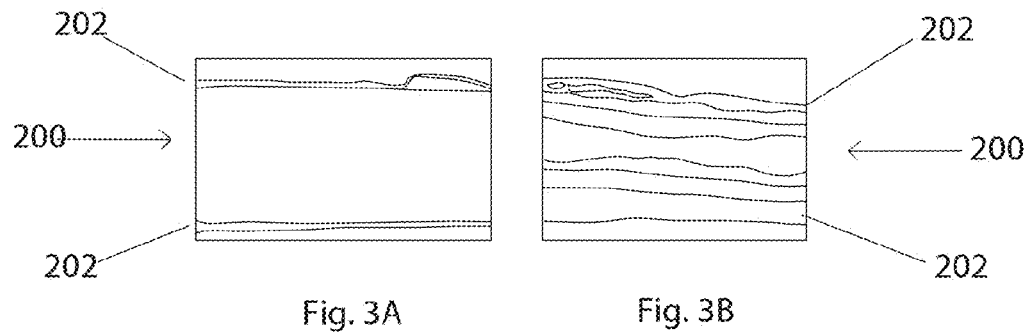
FIGS. 3A and 3B shows two longitudinal sections of allograft fiber material after 3 and 6 weeks of culturing with cells according to the state of the art. Differing in magnification, no apparent difference in size was evident despite the much thicker matrix that attached to the NDGA-treated fibrils.
Figure 4:
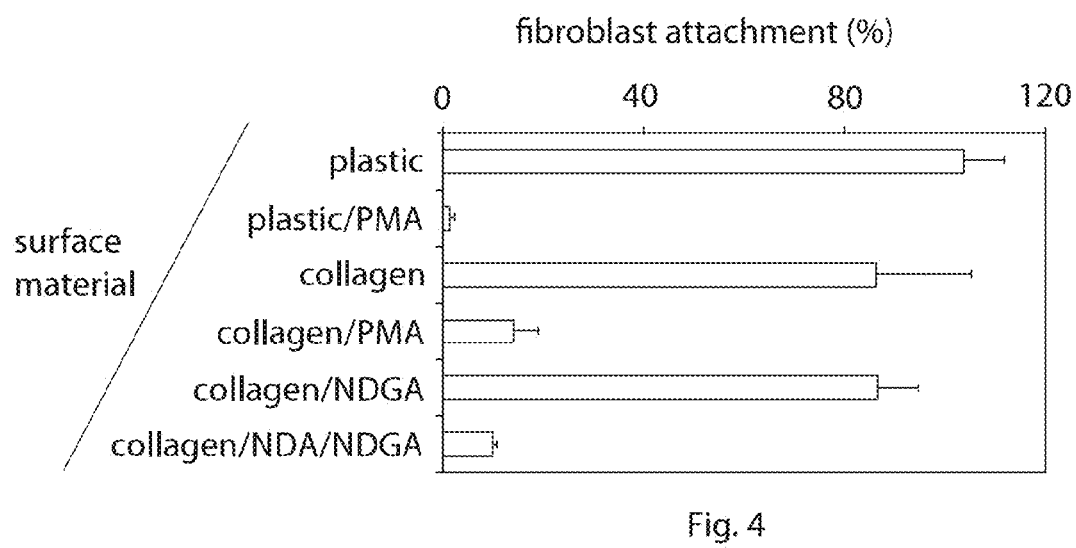
FIG. 4 shows the fibroblast attachment to tissue-culture treated dishes coated with collagen, and collagen-coated dishes treated with NDGA. The number of cells attached following removal of unattached cells with Dulbecco's PBS measured with CyQuant cell proliferation assay.

With reference to FIGS. 1A-1K, a number of perspective views of exemplary synthetic metallic or combinations thereof of some typical implants 10 that are made according to the present invention are illustrated. Each of the implants 10 as shown has a metallic, synthetic or combination of metallic and synthetic implant body structures 12. The implant body structures 12 as shown are designed for insertion on or into a skeletal spinal structure of a patient. FIG. 1A is the Phenix CID, FIG. 1B is the Talos-P PLIF, FIG. 1C is the TLIF, FIG. 1D is Talos-T TLIF, FIG. 1E is entitled OLIF, FIG. 1F is Talos-A ALIF, FIG. 1G is LLIF, FIG. 1H is Thor Standalone ALIF, FIG. 1I is the Diamond Cervical Plate, FIG. 1J is the Facet Screw Skirt and FIG. 1K is a synthetic woven pouch used in bone grafting and repair. These devices are simply examples and not intended to be limiting in any way.

Each of these exemplary spinal implant device examples are manufactured and sold by Amendia or are competitor's alternatives that are also available for this purpose. For the purposes of simplification, each of these devices are commonly referred to by reference numeral 10 for the device and 12 for its body structure even though they are structurally not the same in appearance each device 10 shown in FIGS. 1A-1K is designed to function as a spinal implant device made in accordance to the present invention.

With reference to FIG. 1A, the Phenix CID, Phenix™—Cervical Interbody Device: Is a rectangular implant comprised of PEEK-OPTIMA® polymer from Invibio Biomaterial Solutions, a radiolucent material with properties that match the modulus of elasticity of cortical bone. The Phenix™ is intended for use with supplemental spinal fixation systems that have been labeled for use in the cervical spine. The Phenix "PEEK-OPTIMA® polymer from Invibio Biomaterial Solutions Cervical Interbody Device is available in a range of sizes and heights to fit any anatomy and includes heights up to 12 mm. Available sizes range from a traditional 12 mm×12 mm implant for small vertebral bodies to a 17 mm wide×14 mm A/P implant that sits at the load bearing perimeter of the vertebral body and contains a large graft window.

With reference to FIG. 1B, the Talos-P PLIF, the Talos®-P is a PEEK-OPTIMA lumbar interbody device for PLIF approach. This cage is available in 3 lengths, 2 widths and a complete range of heights with instrumentation that combines with the Talos®-T in one set to provide a complete Posterior and Transforaminal solution.

With reference to FIG. 1D, the Talos-T TLIF, The Talos®-T is a PEEK-OPTIMA lumbar interbody device for TLIF approach. The Talos-T is a curved cage with a functional system for guiding the implant to a proper position. The instrumentation of the Talos®-T is combined with the Talos®-P instrument set to provide a flexible solution for Posterior and Transforaminal approaches. It includes angled teeth to prevent implant migration, tapered nose aids in insertion and distraction, angled shape improves fit between vertebral bodies, functional tamps to guide implant to proper position and tantalum markers.

With reference to FIG. 1E, the Talos-O OLIF, the Talos®-O is a truly unique percutaneous PEEK-OPTIMA lumbar interbody device that is delivered through an oblique approach. This interbody is delivered through an annular incision that is anterior to the transverse process, and is totally percutaneous. The PEEK-OPTIMA implant distracts and provides unquestioned rigid anterior support for the vertebral body. This oblique approach is achieved for all lumbar segments, including the L5-S1 disc space. Our discectomy instruments work through the small access portal to provide a complete percutaneous discectomy. Implants are available in lengths and heights to accommodate all varieties of lumbar interbody spaces. Features include percutaneous delivery, distraction, intervertebral space, anatomical design for implantation, instrumentation for percutaneous discectomy, tapered shape glides past the nerve root, cannulated delivery that preserves safe pathway to the disc space, angled teeth to prevent implant migration and tantalum markers.

With reference to FIG. 1F, the Talos-A ALIF, the Talos®-A is a traditional ALIF interbody device that is available in a range of sizes to accommodate every anatomic requirement. Instrumentation is provided for delivery from an Anterior or Anterolateral approach. A variety of lordotic angles and sizes are available. It includes chamfered corners provide anatomical fit, angled teeth prevent implant migration, two insertion options for anterior or anterolateral approaches, lordotic angles to match spinal anatomy, implant trials and rasps for preparing disc space and tantalum markers.

With reference to FIG. 1I, the Diamond Cervical Plate, the Diamond Anterior Cervical Plate is a world class cervical plating system utilizing a unique self-locking mechanism that is effortless to engage and offers superior screw retention while providing a simple revision technique. The Diamond Cervical Plate is offered in single through four level varieties and has the option of fixed or variable screws, and self-tapping or self-drilling. Rescue screws are also provided. Benefits include; superior back-out resistance, fixed and variable screws for rigid, dynamic, or hybrid stabilization, variable screws allow 30 degrees of freedom, low profile, easy to revise, color-coding of screws for length and fixed/variable head identification, instrumentation designed to reduce surgical steps, diamond window allows for greater graft visualization and self-drilling tip or conservative self-tapping tip.

FIG. 1K shows a surgical mesh made of a Polyethylene Terephthalate (PET) mesh pouch designed to contain impacted granular bone graft and enable its incorporation. The mesh is used most commonly for traumatic fracture repair and interbody fusion.

As shown in FIGS. 1A through 1H, each of the body structures 12 is provided with at least one vertically oriented channel 16 or aperture which extends through the implant device 10. These channels 16 are provided to enable bone tissue or bone graft material to be inserted into the device during a surgical procedure. Some of the exemplary embodiments have a lateral or side opening or channel 18. The side openings or channels 18 are provided to enable an x-ray to pass through the implant device in order to establish bone formation in the patient after surgery has been completed and the implant has been inserted for a period of time. Additionally, some implants 10 may have holes 15 such as in the diamond cervical plate 10 of FIG. 1I threaded or otherwise to allow the device 10 to be secured or anchored to the spinal skeleton structure between adjacent vertebrae if so desired. Several of the devices are shown with jagged or toothed outer surface 17 on the upper surface 11 and lower surface 13, these features help the device 10 to engage the vertebrae when implanted and help hold the device 10 into position between adjacent vertebrae during the surgical procedure. The exterior surface of the body structures 12 of each of these devices can be coated with a coating 22 gel or spray of a biological substance or material containing stem cells 21 when made according to the present invention.

Alternatively, as illustrated in FIG. 2, a sheet 2 of material can be provided that has the pattern 100A on a collagen layer 10A. This sheet 2 can be wrapped around each of the exemplary implant devices 10 at the time of surgery if so desired. This is illustrated in FIG. 6. Alternatively, as will be discussed later the sheet 2 can form a wrap around the implant device 10 which can be pre-assembled at a manufacturing facility in a sterile environment, packaged and shipped to the medical facility for direct use as a surgical implant with a sheet 2 material wrapped about the outer surface of the implant device 10. It is this combination of the implant device 10 with a sheet of material 2 that provides an enhanced ability of the implant to be accepted by the patient in order for the implant to be fused by enhanced bone growth between vertebrae if so desired. Ideally as previously discussed, the implant device 10 also has the pattern 100A on the exposed surface 13 wrapped by the sheet 2. This combination provides a large bone growth enhancing surface between the device 10 and the sheet 2 to promote bone growth.

Typically the channels 101 having exposed surfaces with the pattern 100A of the implant devices 10 can be filled with bone graft material either in a paste form or in solid bone material. This material during the patient's healing is expected to fuse with the adjacent vertebrae and by providing an envelope or covering so that the implant device 10 will be more quickly fused to the spinal skeletal structure in a faster more rapid fashion due to the ability of the cells to trigger the regenerative process and to allow the adjacent bone structure to grow around the implant device more quickly than would occur otherwise in the absence of the material 2.

Figure 8:
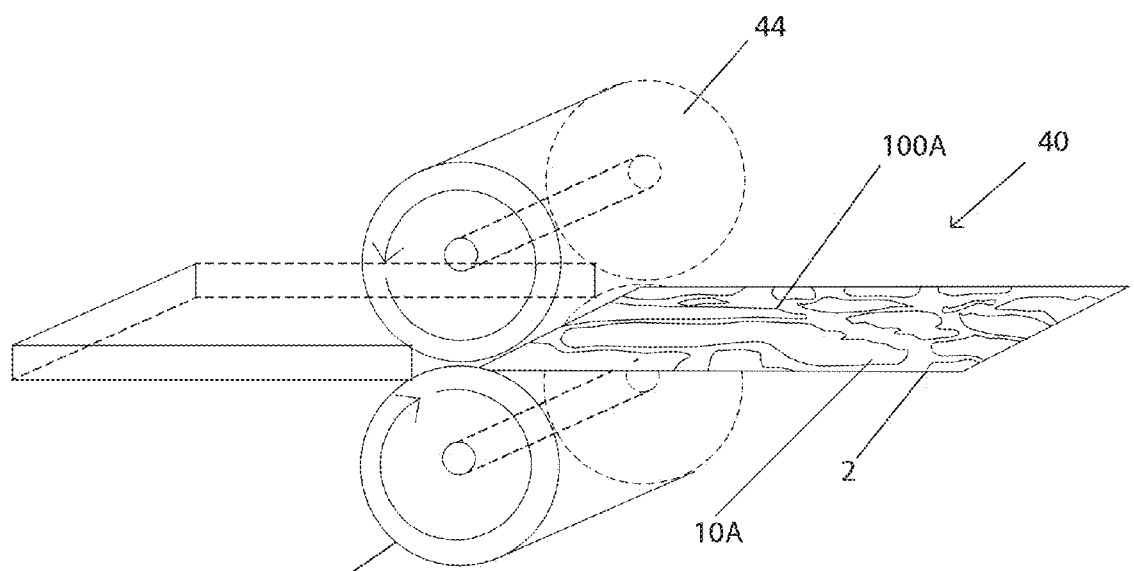
FIG. 8 shows a schematic drawing of a device for producing a sheet material according to the present invention by rolling.
Figure 9:
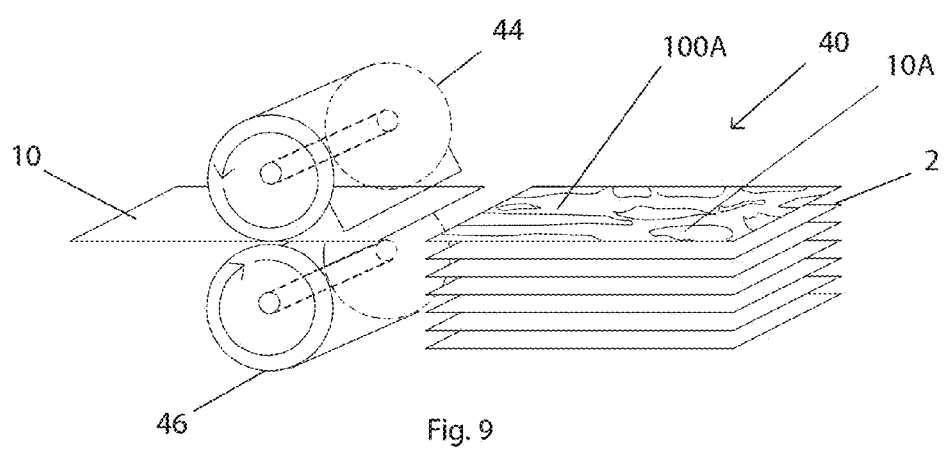
FIG. 9 shows another schematic drawing of the device according to FIG. 8, further equipped for producing thin wafer material for producing a sheet material laminate.

Advancements in technology and refinements in application now permit reproducible templates of geometric patterns to be made with 10-micron resolution. Based on high resolution micro-CT analysis of blocks of whale bone (Microphotonics, Inc., Allentown, Pa.) surface material can now be reproducibly made that replicate the cancellous morphology of under-modeled mammalian bone (FIG. 2) using template driven masking (Intelligent Micropatterning, LLC, St. Petersburg, Fla.). Advancements in technology and refinements in application now permit reproducible templates 100A of collagen to be made with 10-micron resolution. Based on high resolution micro-CT analysis of blocks of whale bone (Microphotonics, Inc., Allentown, Pa.), and Micro-CT Center, UCONN Health Center), planar stacks of material 10 can now be reproducibly made that replicate the cancellous morphology of under-modelled mammalian bone, as shown in FIG. 2, using template 100A driven compression molding derived from patterns 100A detailed (Intelligent Micropatterning, LLC, St. Petersburg, Fla.) and etchings defined in metal masters rollers 44, 46 (Akron Metal Etching, Co., Akron, Ohio) as shown in FIGS. 8 and 9 material 40 can be achieved repeatedly in sheets or layers 2. Among the recently developed scaffolds for tissue engineering, polymeric hydrogels have proven satisfactory in cartilage and bone repair and can be used in combination with the present implant device. Peptide self-assembly has been shown to be a useful tool for the preparation of bioactive nanostructures, and recent work has demonstrated their potential as therapies for regenerative medicine and this technology can be applied to the present invention as well. Using amphiphilic molecular domains, either as primary links, or by incorporating known enzymatic cleavage strategies, it is possible to accentuate surface charge potential and thereby heighten the response to regenerative challenge.

Table 2 is the morphometric data of human cancellous bone samples H-1-H4 and whale cancellous bone W1. Briefly the entire specimen was imaged and the whale bone was purposely cut large to look for the internal consistency of the form to follow variation in scales of sizing. The cancellous bone samples range from 1-4 also in order of being most osteoporotic (1) and the number (4) specimen being the most normal bone. Number 3 specimen is likely an outlier and might sit adjacent to a cortical margin. The whale bone is consistent independent of boundary range or isometric randomization to size. The value in the whale bone is to isotropic distribution, thicker trabecula, greater trabecular spacing, and highest tissue density with lowest connectivity for equalized total volume. The importance is ridge dynamics, higher density with lesser void despite having greater separation makes this an ideal pattern for mimicking to enhance new bone growth in humans.

TABLE 2

| Sample No. | BVF (BV/TV) | Trab. Thickness μm | Trab. Number 1/mm | Trab. Spacing μm | Connec. Density 1/mm$^3$ | Apparent Density Mg/ccm HA | Tissue Density Mg/ccm HA | Total Volume mm$^3$ | Bone Volume mm$^3$ | SMI | Bone Surface mm$^2$ | BS/BV mm$^2$ | BS/TV 1/mm | BS/MV 1/mm | DA |
|---|---|---|---|---|---|---|---|---|---|---|---|---|---|---|---|
| | | | | | Just within boundaries of pieces | | | | | | | | | | |
| H1 | 14.0% | 142 | 1.41 | 653 | 6 | 65 | 888 | 570.999 | 83.594 | 1.7 | 1595.7 | 19.0 | 2.8 | 3.3 | 1.6 |
| H2 | 21.0% | 146 | 1.69 | 521 | 7 | 149 | 869 | 541.047 | 113.830 | 0.8 | 1989.8 | 17.2 | 3.7 | 4.7 | 2.8 |
| H3 | 24.0% | 191 | 1.65 | 525 | 6 | 185 | 917 | 417.510 | 100.217 | 1.0 | 1399.6 | 13.8 | 3.4 | 4.4 | 1.6 |
| H4 | 31.7% | 156 | 2.24 | 374 | 17 | 286 | 891 | 380.271 | 120.339 | 0.3 | 1908.7 | 15.6 | 6.0 | 7.3 | 1.7 |
| Wt | 21.1% | 183 | 1.20 | 800 | 3 | 190 | 866 | 1070.286 | 225.320 | 0.4 | 3126.6 | 13.7 | 2.9 | 3.7 | 1.4 |

TABLE 2-continued

| Sample No. | BVF (BV/TV) | Trab. Thickness μm | Trab. Number 1/mm | Trab. Spacing μm | Connec. Density 1/mm^3 | Apparent Density Mg/ccm HA | Tissue Density Mg/ccm HA | Total Volume mm^3 | Bone Volume mm^3 | SMI | Bone Surface mm^2 | BS/BV mm^2 | BS/TV 1/mm | BS/MV 1/mm | DA |
|---|---|---|---|---|---|---|---|---|---|---|---|---|---|---|---|
| Smaller isometric cube ROI | | | | | | | | | | | | | | | |
| H1 | 15.9% | 139 | 1.63 | 578 | 6 | 87 | 890 | 70.113 | 11.152 | 1.9 | 208.8 | 18.9 | 3.0 | 3.5 | 1.6 |
| H2 | 24.0% | 160 | 1.80 | 488 | 8 | 186 | 871 | 70.113 | 16.798 | 0.8 | 277.5 | 16.4 | 4.0 | 5.2 | 2.4 |
| H3 | 26.3% | 174 | 1.78 | 487 | 8 | 218 | 911 | 70.113 | 18.451 | 0.9 | 266.0 | 14.4 | 3.6 | 5.1 | 1.7 |
| H4 | 24.0% | 156 | 2.36 | 360 | 18 | 319 | 882 | 70.113 | 24.256 | 0.0 | 372.6 | 15.2 | 5.3 | 8.1 | 1.7 |
| Wt | 21.1% | 167 | 1.29 | 768 | 3 | 226 | 897 | 70.113 | 14.780 | 0.3 | 212.9 | 14.3 | 3.0 | 3.8 | 1.5 |
| Smallest isometric cube ROI | | | | | | | | | | | | | | | |
| H1 | 16.6% | 144 | 1.63 | 577 | 5 | 94 | 892 | 45.084 | 7.457 | 1.8 | 134.3 | 18.1 | 3.0 | 3.6 | 1.6 |
| H2 | 24.9% | 152 | 1.88 | 471 | 8 | 194 | 870 | 45.084 | 11.219 | 0.8 | 180.5 | 16.1 | 4.0 | 5.3 | 2.3 |
| H3 | 26.6% | 173 | 1.82 | 475 | 7 | 221 | 908 | 45.084 | 11.993 | 0.9 | 172.6 | 14.4 | 3.8 | 5.2 | 1.8 |
| H4 | 35.3% | 155 | 2.41 | 352 | 19 | 326 | 880 | 45.084 | 15.903 | −0.1 | 243.7 | 15.2 | 5.4 | 5.4 | 1.7 |
| Wt | 20.4% | 166 | 1.32 | 754 | 3 | 220 | 902 | 45.084 | 9.178 | 0.4 | 134.6 | 14.6 | 3.0 | 3.7 | 1.5 |

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. The method of producing a bone implant having a solid body structure having exposed surfaces; the method comprises the step of creating a bone formation enhancing 3-dimensional pattern by one of molding, etching, embossing, machining, masking, plasma deposition, plasma enhanced chemical deposition, additive fabrication, lasering, or assembling of layers of the pattern into one or more selected portions of the exposed surfaces; and wherein the one or more selected portions of the exposed surfaces having a porosity created by having the bone formation enhancing geometric 3-dimensional pattern duplicating or replicating the cancellous morphology of under-modelled pre-natal bone compared to an adult human bone by mimicking a marine or sea mammal bone structure or a pre-natal human bone structure wherein the bone formation enhancing repeatable geometric 3-dimensional pattern mimics or replicates the following characteristics of whale bone;

| BIOPSY | BV/TV | BS/BV | TbTh | TbSp | TbN | Ost # |
|---|---|---|---|---|---|---|
| Cross | 17.71 | 14.98 | 135.16 | 631.70 | 1.33 | 230/mm^2 |
| Long | 24.54 | 8.67 | 231.05 | 710.98 | 1.06 | 150/mm^2. |

2. The method of claim 1 wherein the pattern is repeating.

3. The method of claim 1 wherein the pattern is repeatable.

4. The method of claim 1 wherein the bone formation enhancing geometric 3-dimensional pattern is placed on portions of the exposed surface to create a continuous network having voids having a medium width of 500 to 800 microns formed as a trabecular structure which enhances bone formation, the voids of the continuous network extend to a depth of 150 microns or less from the one or more portions of the exposed selected surface having the 3-dimensional pattern, the depth being the distance the pattern penetrates into the body structure to produce the pattern.

5. The method of claim 1 wherein the exposed surface is on exposed exterior portions of the body structure or on exposed internal portions of the body structure or both.

6. The method of claim 5 wherein the one or more selected portions of the exposed portions having the bone formation enhancing repeatable geometric 3-dimensional patterns are in the external exposed surfaces or in the internal exposed surfaces or both internal and external exposed surfaces.

7. The method of claim 1 wherein the solid body structure is made of an implantable plastic or polymer.

8. The method of claim 7 wherein the plastic is PEEK.

9. The method of claim 1 wherein the solid body structure is made of a metal suitable for implanting in a human or mammal.

10. The method of claim 9 wherein the metal is titanium or a titanium alloy.

11. The method of claim 9 wherein the metal is stainless steel or a stainless steel alloy.

12. The method of claim 7 wherein the plastic material can be any implantable grade material such as PEEK (polyether ether ketone), PEKK (polyether ketone ketone), polyethylene, ultra high molecular weight polyethylene, polyphenylsulfone, polysulfone, polythermide, acetal copolymer, polyester woven or solid or implantable grade lennite UHME-PE.

13. The method of claim 1 may include anchoring holes to secure the device to the skeletal structure with fasteners or alternatively can simply be held in place by and between adjacent skeletal structures.

14. The method of claim 1 wherein the sea or marine mammal is a whale.

15. The method of claim 1 wherein the sea or marine mammal is a dolphin.

16. The method of claim 1 wherein the implant at select portions exhibits a stress neutral isotropic structure for enhancing bone formation.

17. The method of claim 1 wherein the solid body structure is made of bone allograft.

* * * * *